United States Patent [19]
Renirie

[11] Patent Number: 5,814,087
[45] Date of Patent: Sep. 29, 1998

[54] RATE RESPONSIVE PACEMAKER ADAPTED TO ADJUST LOWER RATE LIMIT ACCORDING TO MONITORED PATIENT BLOOD TEMPERATURE

[75] Inventor: Alexis C. M. Renirie, Berg en Dal, Netherlands

[73] Assignee: Medtronic, Inc., Minneapolis, Minn.

[21] Appl. No.: 768,604

[22] Filed: Dec. 18, 1996

[51] Int. Cl.⁶ .................................................. A61M 1/36
[52] U.S. Cl. ................................. 607/21; 607/18; 607/17
[58] Field of Search .................................. 607/17, 18, 21

[56] References Cited

U.S. PATENT DOCUMENTS

| | | | |
|---|---|---|---|
| 3,867,950 | 2/1975 | Fischell | 607/33 |
| 4,436,092 | 3/1984 | Cook et al. | 607/21 |
| 4,543,954 | 10/1985 | Cook et al. | 607/21 |
| 4,719,920 | 1/1988 | Alt et al. | 607/21 |
| 4,803,987 | 2/1989 | Calfee et al. | 607/21 |
| 4,905,697 | 3/1990 | Heggs et al. | 607/18 |
| 4,945,909 | 8/1990 | Fearnot et al. | 607/18 |
| 4,995,390 | 2/1991 | Cook et al. | 607/21 |
| 5,005,574 | 4/1991 | Fearnot et al. | 607/21 |
| 5,029,582 | 7/1991 | Lekholm | 607/21 |
| 5,336,244 | 8/1994 | Weijand . | |
| 5,376,106 | 12/1994 | Stahmann et al. . | |
| 5,476,483 | 12/1995 | Bornzin et al. | 607/17 |
| 5,645,576 | 7/1997 | Limousin et al. | 607/19 |

OTHER PUBLICATIONS

Case Studies on the Effect of Exercise and Hot Water Submersion on Intracardiac Temperature and the Performance of a Pacemaker Which Varies Pacing Rate Based on Temperature (Neal E. Fearnot, Ph.D., Osamu Kitoh, M.D., Tamotsu Fujita, M.D., Hiroshi Okamura, M.D., Heidi J. Smith, Ph.D., Mark Calderini)–Japan Heart J. 30(3):353–63. May 1989.

Overnight Heart Rate and Cardiac Function in Patients with Dual Chamber Pacemakers (Paul H. Chew, David E. Bush, Bernard T. Engel, Mark I. Talan and R. Tracy Abell)— PACE, vol. 19(5) May 1996.

Evaluation of Rate–Responsive Pacemakers by Transesophageal Holter Monitoring of Spontaneous Atrial rate (Maria Grazia Bongiorni, Ezio Soldati, Luca Paperini, Andrea Pozzolini, Dianora Levorato, Guiseppe Arena, Paolo Pistelli, Gianluga Quirino, Andrea Biagini, and Carlo Contini)— PACE, vol. 13 (12) Dec. 1990, Part II.

*Primary Examiner*—William E. Kamm
*Assistant Examiner*—Carl H. Layno
*Attorney, Agent, or Firm*—Michael J. Jaro; Harold Patton

[57] ABSTRACT

A rate responsive pacemaker is provided having the capability of automatically adjusting the lower rate limit (LRL) for sleep, or nighttime. The pacemaker has a temperature sensor for determining patient blood temperature, and processes patient blood temperature data to obtain an average daily low value of nighttime blood temperature. The pacemaker monitors blood temperature to determine a drop below a threshold which is coupled to the average daily low value, as well as when the rate of temperature change exceeds a predetermined limit, these two coincident conditions suggesting onset of nighttime and/or sleep. Lower rate limit is decremented, preferably by a predetermined amount at onset of nighttime, and is automatically incremented when patient blood temperature and/or time of day indicate the end of nighttime.

15 Claims, 3 Drawing Sheets

RATE RESPONSIVE PACEMAKER ADAPTED TO ADJUST LOWER RATE LIMIT ACCORDING TO MONITORED PATIENT BLOOD TEMPERATURE

FIELD OF THE INVENTION

This invention relates to rate responsive pacemakers and, in particular, pacemakers having an adjustable lower rate limit.

BACKGROUND OF THE INVENTION

Rate responsive pacemakers are well known and widely used in the art. In a rate responsive pacemaker, one or more parameters reflecting desired pacing rate are sensed and utilized by the pacemaker for controlling the rate of generated and delivered pacing pulses. For example, it is well known to use a sensor which measures the activity of the patient, and translate a measure of patient activity into pacing rate, such that the pacemaker rate essentially tracks the activity of the patient. Other parameters are known to be indicative of pacing rate, e.g., monitored blood temperature and Q-T interval. Further, it is known to use plural sensors, whereby two or more parameters are monitored and incorporated in an appropriate algorithm for determining pacing rate.

In any rate responsive pacemaker, limits must be set on the excursion of the pacing rate. As is understood in the art, the pacing rate cannot be driven too high, and accordingly, an upper rate limit (URL) is set such that any attempt to pace above this URL will be denied. Likewise, the patient should not paced at too low a rate, even when at rest and even when at sleep, and accordingly, a lower rate limit (LRL) is likewise set. The LRL and URL limits may be programmed by the physician, or may be subject to automatic adjustment.

It is desirable, for several reasons, to adjust LRL downward, or decrement LRL, when the patient is sleeping at night. When sleeping, the patient simply doesn't need to have his or her heart paced at the rate at which it is normally paced during the day. Stated differently, it is desirable that the rate follow the patient's circadian rhythm. Additionally, dropping the pacing rate at night for approximately the duration of the patient's sleep leads to a decrease in the number of pace pulses delivered, and a consequent saving in battery energy and increase in pacemaker lifetime. While there are known pacing systems wherein LRL can be adjusted, and pacing systems which adjust pacing rate for nighttime, there remains a need in the art for improvement in adjusting LRL to correspond to actual patient nighttime conditions.

SUMMARY OF THE INVENTION

In accordance with the above object, there is provided a pacemaker system having a rate responsive pacemaker, and control means for controlling the rate limits within which pacing rate can be varied in response to changing patient conditions. In particular, the pacemaker of this invention has the capability of tracking patient blood temperature and determining a measure of the average daily low nighttime blood temperature of the patient. The pacemaker also periodically makes a determination of the time rate of change of blood temperature, to determine whether there has been a change in both magnitude and rate which corresponds to nighttime rest. When these blood temperature conditions and actual nighttime are found to coincide, the lower rate limit is decremented to a value more corresponding to a desired nighttime pacing rate. The pacemaker continues to monitor time and patient conditions through nighttime, and readjusts LRL upward at an appropriate time, corresponding either to the end of a time duration corresponding to average sleep length or corresponding to increased activity as indicated by rising blood temperature.

DESCRIPTION OF THE PREFERRED EMBODIMENTS

Figure 1:
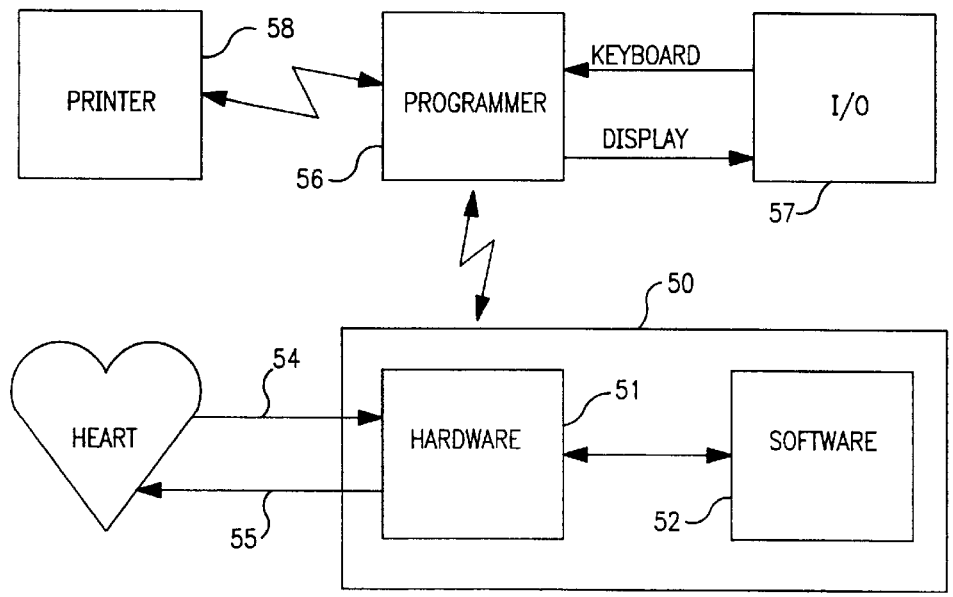
FIG. 1 is a block diagram of the overall system of the invention, showing the environment in which the pacemaker operates.

The pacing system of this invention is preferably software-based, i.e., the software controls functions through hardware, as illustrated in FIG. 1. Referring specifically to FIG. 1, a pacemaker 50 is shown as having a component hardware portion 51 and a software portion 52, the two portions being interconnected. The software is parameter-driven, i.e., there are numerous parameters that control the pacing behavior, diagnostic functions, etc. The hardware is interconnected with the patient's heart by one or more electrodes 55, and one or more sensor connections 54, for developing a rate response control signal. As is well understood in the art, for a dual chamber pacemaker, there are generally two leads, an atrial lead and a ventricular lead, each lead having at least one electrode, unipole or bipole, positioned in the heart. The line 54 is illustrated as leading to the heart, as in a QT-type sensor arrangement, but may be attached to the outside case of the pacemaker or may couple to any other available sensors for sensing body parameter information used in rate responsive pacing systems.

As further illustrated in FIG. 1, the pacer 50 is in telemetric communication with a programmer 56. The user can select parameters and program them through programmer 56, and can also interrogate parameter and diagnostic data from the implanted pacemaker. Interrogated information from the pacer can be coupled by telemetry directly to a printer 58. Input/output devices 57 are used to input information by the user to the programmer, or to display information received by the programmer from the pacemaker.

Figure 2:
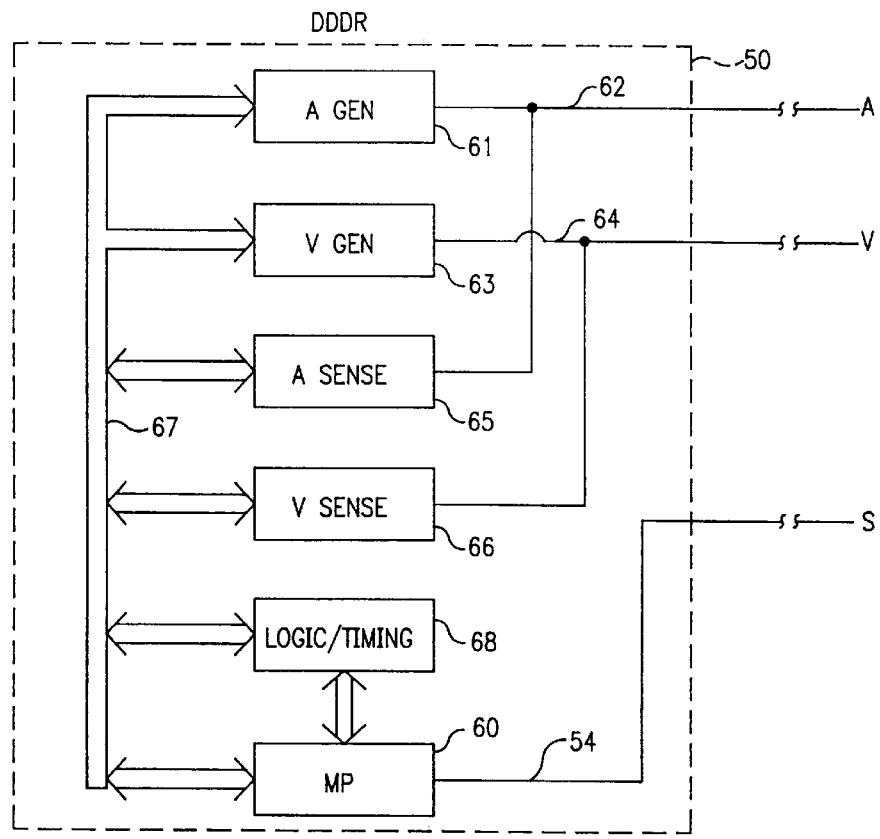
FIG. 2 is a block diagram which illustrates basic components of the pacemaker of this invention, together with leads and a sensor for delivering signals to and/or receiving signals from the patient.

Referring to FIG. 2, there is shown a basic block diagram of primary hardware components of a DDDR pacer 50. Although the subject invention is illustrated with respect to ventricular pacing, a dual chamber DDDR pacer is illustrated, since the invention can be practiced with a dual or single chamber pacer. An atrial generator 61 is shown, having an output connected to lead 62 which communicates with the patient's atrium. An A-sense amplifier 65 is illustrated also connected to atrial lead 62. A ventricular generator is illustrated which is connected to the patient's ventricle through lead 64. V-sense amplifier 66 is also connected to lead 64, to receive and sense signals from the patient's ventricle. Generators 61 and 63 and sense blocks 65 and 66 are interconnected with microprocessor system 60, which microprocessor has software which is parameter-driven to control the operation of the hardware units. Microprocessor system 60 may be interconnected with hardware logic and/or timing circuits 68. As affects the scope of this invention, the degree to which software supplants hardware, or vice versa, is a matter of design choice. Thus, for the timing functions that are carried out in the pacing system of this invention, it is to be understood that the microprocessor may have built in timing circuits, or suitably may control external hardware timer circuits. Software control of pacing function, and specifically setting pacing rate limits, is well known in the art, such that the following detailed discussion of an illustrative software routine enables one of ordinary skill in this art area to design a system for carrying out the invention. Data inputted from programmer 56 is stored in memory associated with microprocessor 60.

Still referring to FIG. 2, there is shown a sensor S indicated as providing an input to microprocessor system 60. Sensor S, in the preferred embodiment of this invention, represents a blood temperature sensor, such as is known in the art, for obtaining a signal which carries information indicative of patient blood temperature.

Figure 3A:
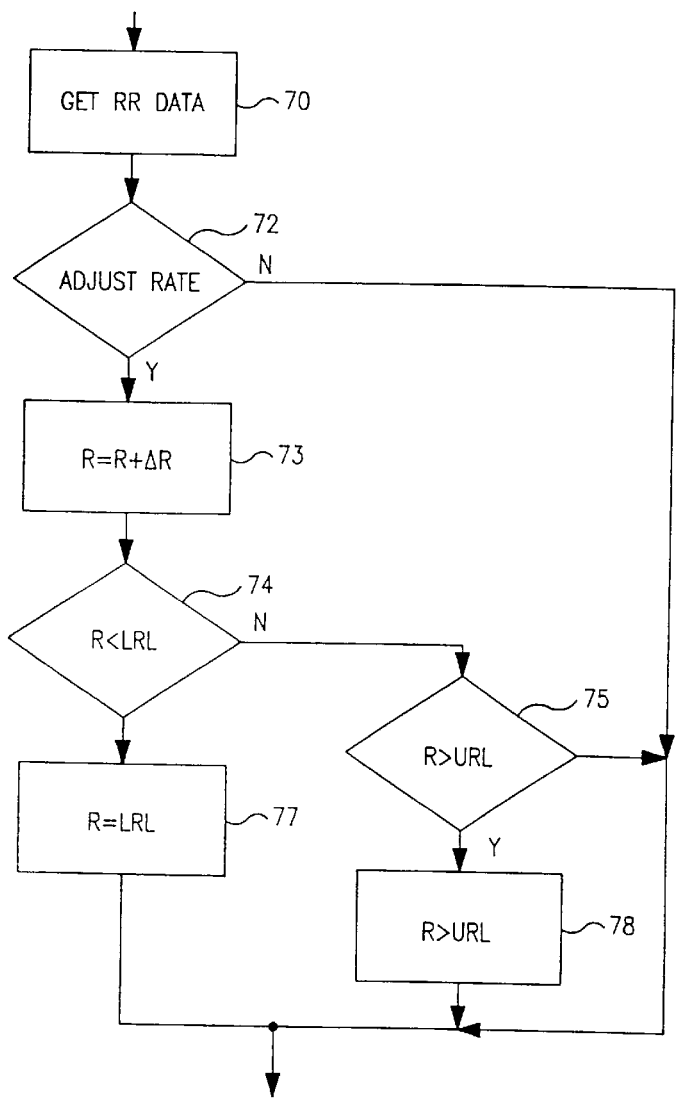
FIG. 3A is a simple flow diagram showing the steps taken in a conventional pacemaker for adjusting rate within a lower rate limit (LRL) and an upper rate limit (URL)

Referring now to FIG. 3A, there is shown a flow diagram of steps taken to adjust the pacing rate in a conventional pacemaker. At 70, rate response data is obtained, typically each cycle. The rate response data may be any parameter such as activity, blood temperature, Q-T interval, etc., as is known in the art. At 72, it is determined whether the rate should be adjusted. If yes, at 73 the rate is adjusted by $\Delta R$, which may be up or down. Following the adjustment, at 74 and 75 the pacemaker checks to see whether the calculated adjusted rate is below LRL or above URL. If, at 74, R is found to be below LRL, R is reset to LRL. Likewise, if at 75 R is found to be above URL, then at 78 the rate is set to the value of URL. At set forth above, the improvement of this invention is in setting the value of LRL as a function of blood temperature, to provide specifically for decrementing LRL during nighttime or sleep.

Figure 3B:
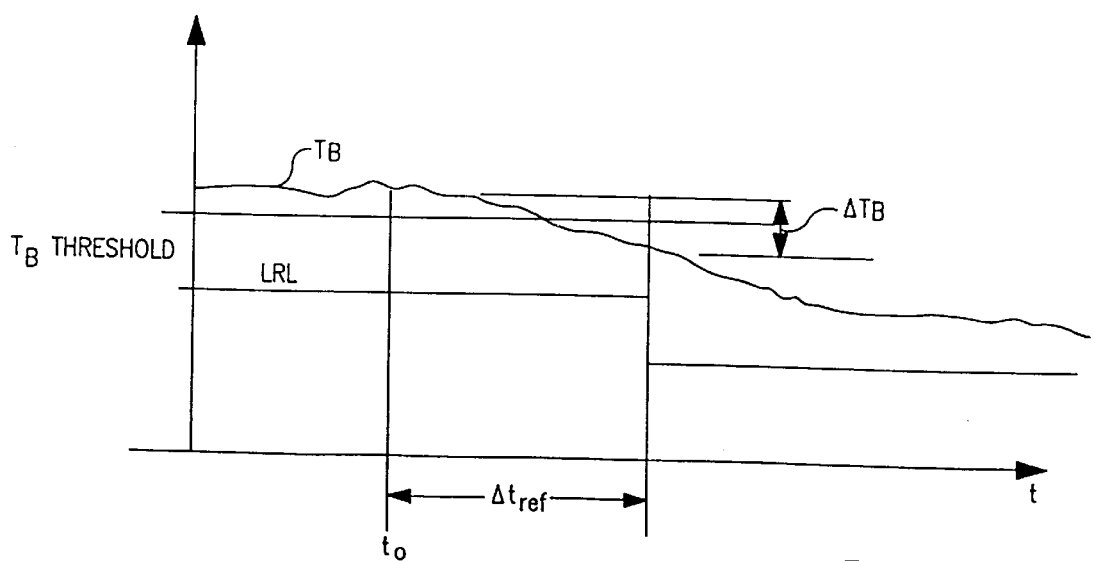
FIG. 3B is a set of curves demonstrating how LRL is adjusted as a function of change in blood temperature, in accordance with this invention.

Referring to FIG. 3B, there is shown a plot of blood temperature ($T_B$) as a function of time. There is a corresponding plot of LRL. At time $t_0$, the pacemaker initiates time out of a next time interval designated as $\Delta t_{ref}$. The value of $\Delta t_{ref}$ may be programmed at, e.g., 30 minutes, or that every 30 minutes the pacemaker will check blood temperature conditions to determine whether it is appropriate to drop LRL. During the time out of $\Delta t_{ref}$ the blood temperature $T_B$ is shown as decreasing. At the end of $\Delta t_{ref}$, $T_B$ is shown as being below the $T_B$ Threshold, which has previously been determined in accordance with this invention. Further, there is indicated a value $\Delta T_B$, where the ratio of $\Delta T_B$ to $\Delta t_{ref}$ is a measure of the recent rate of decrease of blood temperature. As discussed in more detail in connection with FIGS. 4A and 4B below, the pacemaker of this invention comprises software or other logic for comparing blood temperature with the blood temperature threshold and for determining whether the time rate of change of blood temperature has exceeded a predetermined rate. If both of these comparisons have occurred, it can reasonably be concluded that the patient has entered a period of nighttime rest such that LRL can be dropped.

Figures 4A, 4B:
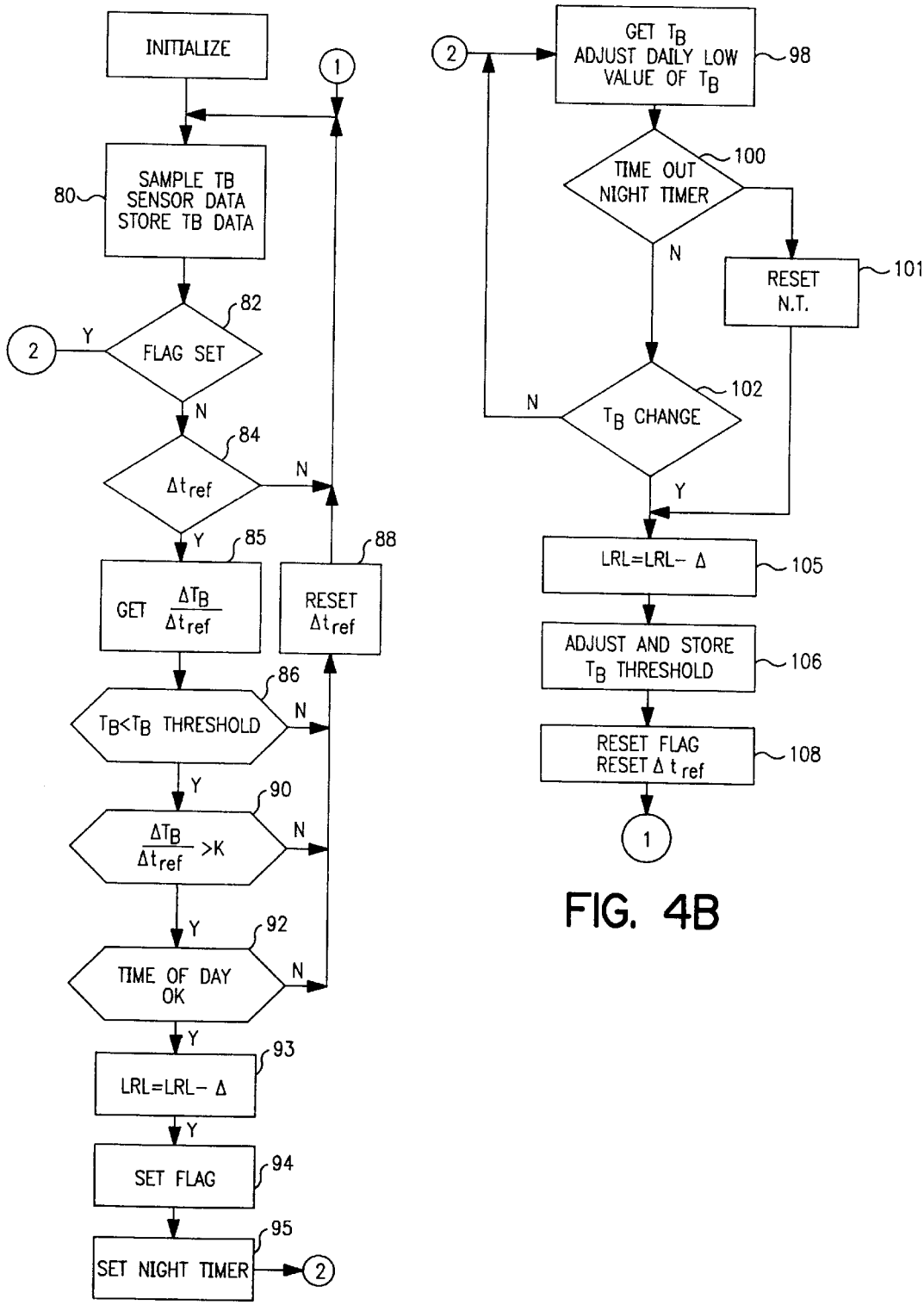
FIG. 4A is a first flow diagram of a routine in accordance with this invention for adjusting LRL as a function of blood temperature ($T_B$)
FIG. 4B is a second portion of the routine for adjusting LRL as a function of $T_B$.

Referring now to FIG. 4A, there is shown a flow diagram illustrating basic steps in the pacemaker routine for adjusting LRL downward during nighttime rest. At 80, the pacemaker samples $T_B$ sensor data, and stores the $T_B$ data. This step can be taken cyclically, i.e., every pacemaker cycle, or less frequently if desired. At 82, the routine checks to see whether the nighttime flag has been set. If no, at 84 the pacemaker determines whether the time period $\Delta t_{ref}$ has timed out. If no, the routine loops back to 80. However, if it has timed out, at 85 the ratio $\Delta T_B/t_{ref}$ is determined. Then, at 86, the routine compares $T_B$ to see if it is less than $T_B$ Threshold. If no, a criterion for lowering LRL at night has not been met, and the routine goes to 88 where the $\Delta t_{ref}$ timer is reset; the routine then loops back to block 80. If the answer at 86 is yes, the routine goes to 90, where it compares the ratio of $\Delta T_B$ to $\Delta t_{ref}$ with a predetermined constant K. If this ratio is less than K, the routine loops back through block 88. If it is greater than K, meaning that the rate of drop is at least a predetermined rate corresponding to the condition of patient sleep, the routine goes to 92. At this point, as an optional feature, a time of day clock may be monitored to see if the time of day in fact is within nighttime. If no, LRL is not lowered, the routine again looping back through 88 to 80. However, if the time of day does correspond to nighttime, the routine goes to 93 and decrements LRL by a predetermined value designated as $\Delta$. Following this, at 94 the flag is set, to indicate that a condition of lowered LRL at nighttime exists. At 95, a night timer is set. The night timer may be set at any predetermined duration, e.g., 6–8 hours, to give an indication of when the lowered LRL has been set for approximately a normal nights' sleep for the patient. Referring now to FIG. 4B, corresponding to the nighttime condition of lowered LRL, at 98, the pacemaker periodically monitors the value of $T_B$, e.g., pacemaker cycle. Each value of $T_B$ is compared with the lowest value of $T_B$ stored for the current night, and the daily low value of the $T_B$ is determined. At block 100 the pacemaker checks to see whether the night timer has timed out. If it has, then it is reset at 101, and the routine goes to 105 and adjusts LRL back upward by $\Delta$, since a reasonable period of nighttime activity has now expired. If, at 100, the night timer has not timed out, at 102 it may be determined whether there has been a change in blood temperature, e.g., a rise of blood temperature back up above the threshold. If no, the routine loops back to 98. If yes, the assumption is that the rise in blood temperature corresponds to patient activity, and at 105 LRL is incremented. After this at 106, the daily low value of $T_B$ is obtained, and used to update a running average daily low value of $T_B$. From this, an adjusted $T_B$ threshold is obtained and stored. $T_B$ Threshold is suitably maintained slightly above the running average daily low, but in any event is coupled to such average daily low. Following this, at 108 the flag and $\Delta t_{ref}$ are reset, and the routine goes back to [1].

It is thus seen that there is provided a pacemaker having the feature of automatically decrementing LRL in response to nighttime indications. When indications point to the end of patient nighttime, LRL is incremented.

What is claimed is:

1. A rate responsive pacemaker, having a controllable pulse generator for delivering pacing pulses, rate means for sensing at least one parameter containing information indicative of desired pacing rate and control means for controlling said pulse generator to deliver pacing pulses at a rate which is a function of said at least one parameter, said control means further comprising limit means for limiting rate pacing adjustment between a low rate limit (LRL) and an upper rate limit (URL), and having LRL means for adjusting said LRL, said LRL means having a temperature sensor for determining patient blood temperature, measure means for determining from said patient blood temperature a measure of the daily low value of said blood temperature, means for determining a threshold temperature at a predetermined relation to said measure of daily low value, comparison means for continually comparing said blood temperature with said threshold, and up/down adjusting means for adjusting said LRL as a function of said comparison.

2. The pacing system as described in claim 1, wherein said measure means comprises means for determining patient average daily low blood temperature.

3. The pacing system as described in claim 1, wherein said measure means comprises means for storing low temperature values over a predetermined number of days, and averaging means for cyclically determining an average daily low temperature.

4. The pacing system as described in claim 1, comprising change means for determining incremental change in blood temperature over a predetermined increment of time, and means for enabling said LRL adjustment only when said incremental temperature change over said increment of time exceeds a predetermined value.

5. The pacing system as described in claim 1, comprising means for adjusting said threshold in coupled relation to said measure of average daily low value.

6. The pacing system as described in claim 1, comprising timing means for tracking the time of day, and means for enabling said LRL adjustment downward only during a predetermined range of time during a given day.

7. The system as described in claim 1, wherein said adjusting means comprises means for adjusting said LRL downward by a predetermined increment when said blood temperature falls below said threshold.

8. The system as described in claim 1 comprising means operative after said LRL has been adjusted downward for determining when said LRL is to be readjusted upward, and for re-adjusting said LRL upward in response to a said upward determination.

9. The system as described in claim 8, wherein said upward means comprises a nighttime clock for timing out a predetermined night time duration.

10. A rate responsive pacemaker system, having a controllable pulse generator for producing and delivering pace pulses, rate means for sensing at least one parameter containing information indicative of desired pacing rate and control means for controlling the rate of delivery of pace pulses as a function of said at least one parameter, said control means further comprising limit means for limiting rate pacing adjustment to rates above a low rate limit (LRL), and having LRL means for adjusting said LRL, said LRL means further comprising:

a temperature sensor for determining patient blood temperature, threshold means for setting a low blood temperature threshold, said threshold means comprises low temperature means for determining patient daily average low blood temperature;

temperature rate means for determining a measure of the rate of drop of patient blood temperature, determining means for determining the occurrence when patient blood temperature has fallen below said temperature threshold and said rate of drop has exceeded a predetermined rate, and initiating means for initiating a drop of LRL to a lower LRL when a said occurrence is determined.

11. The system as described in claim 10, wherein said LRL means comprises upward adjustment means for adjusting said LRL upward upon the occurrence of predetermined conditions while at a said lower LRL.

12. The system as described in claim 11, wherein said upward adjustment means comprises a clock for timing out a time interval corresponding to a nighttime rest interval.

13. The system as described in claim 10, wherein said low temperature means comprises means for substantially continuously updating said daily average low blood temperature.

14. The system as described in claim 13, comprising means for setting said threshold above said updated daily average low blood temperature.

15. The system as described in claim 10, further comprising clock means for determining nighttime, and said initiating means being inhibited from initiating a drop in LRL except during nighttime.

\* \* \* \* \*